United States Patent [19]

Holzwarth et al.

[11] Patent Number: 5,277,299
[45] Date of Patent: Jan. 11, 1994

[54] PACKAGE FOR MULTIPLE SUTURES

[75] Inventors: Henry A. Holzwarth, Weston; Christopher M. Scanlon, Milford, both of Conn.

[73] Assignee: United States Surgical Corporation, Norwalk, Conn.

[21] Appl. No.: 746,492

[22] Filed: Aug. 16, 1991

Related U.S. Application Data

[63] Continuation-in-part of Ser. No. 629,114, Dec. 17, 1990, abandoned.

[51] Int. Cl.$^5$ ............................................. B65D 85/16
[52] U.S. Cl. ........................... 206/63.3; 206/380; 206/388; 206/476
[58] Field of Search ............ 206/63.3, 227, 363, 206/370, 380, 388, 476

[56] References Cited

U.S. PATENT DOCUMENTS

| | | |
|---|---|---|
| D. 263,505 | 3/1982 | Black . |
| D. 272,600 | 2/1984 | Kubas . |
| 3,136,418 | 6/1964 | Stacy et al. . |
| 3,162,307 | 12/1964 | Regan, Jr. . |
| 3,206,018 | 9/1965 | Lewis et al. . |
| 3,280,971 | 10/1966 | Regan, Jr. . |
| 3,338,019 | 8/1967 | Trewella et al. . |
| 3,338,401 | 8/1967 | Regan, Jr. . |
| 3,363,751 | 1/1968 | Shave et al. . |
| 3,444,994 | 5/1969 | Kaepernik et al. . |
| 3,487,917 | 1/1970 | Shave et al. . |
| 3,490,192 | 1/1970 | Regan, Jr. . |
| 3,545,608 | 12/1970 | Berger et al. . |
| 3,613,879 | 10/1971 | Kemble . |
| 3,627,120 | 12/1971 | Bordeau . |
| 3,759,376 | 9/1973 | Lisowski . |
| 3,779,375 | 12/1973 | Foster . |
| 3,857,484 | 12/1974 | Thyen . |
| 3,939,969 | 2/1976 | Miller et al. . |
| 3,959,947 | 6/1976 | Sonnino . |
| 3,972,418 | 8/1976 | Schuler et al. . |
| 3,985,227 | 10/1976 | Thyen et al. . |
| 4,034,850 | 7/1977 | Mandel et al. . |
| 4,063,638 | 12/1977 | Marwood . |
| 4,089,409 | 5/1978 | Cerwin . |
| 4,120,395 | 10/1978 | Mandel et al. . |
| 4,126,221 | 11/1978 | Cerwin . |
| 4,135,623 | 1/1979 | Thyen . |

(List continued on next page.)

FOREIGN PATENT DOCUMENTS

| | | |
|---|---|---|
| 3027836 | 7/1980 | Fed. Rep. of Germany . |
| 2331638 | 6/1977 | France . |
| 2455880 | 12/1980 | France . |
| 2639215 | 5/1990 | France . |
| 6504467 | 10/1966 | Netherlands . |
| 7302081 | 8/1973 | Netherlands . |
| 680089 | 10/1952 | United Kingdom . |
| 2148232 | 5/1985 | United Kingdom . |
| 2161130 | 1/1986 | United Kingdom . |

Primary Examiner—Jimmy G. Foster
Attorney, Agent, or Firm—Thomas R. Bremer; Peter G. Dilworth; Rocco S. Barrese

[57] ABSTRACT

A suture package is disclosed which is formed of a plurality of panels foldably connected to each other and arranged to fold upon each other to form a suture compartment between pairs of adjacent panels. A generally planar insert member includes portions cut out and lifted from the plane of the insert, respective pluralities of the cut portions being dimensioned and positioned to engage respective portions of a plurality of suture needles positioned thereon to retain the needles in respective fixed spaced positions within the package such that the needles are positioned in one needle compartment and individual flexible suture portions connected to the needles are respectively positioned in individual compartments formed by the remaining adjacent folded panels. In one embodiment portions of certain panels are cut away to reduce the girth of the folded package when loaded. Such portions may either be circular cut-outs or may be provided by dimensioning the length of certain panels less than the others. Apertures are preferably provided to provide access means for packing fluids into the package.

81 Claims, 15 Drawing Sheets

OTHER PUBLICATIONS

| | | |
|---|---|---|
| 4,183,431 | 1/1980 | Schmidt et al. . |
| 4,249,656 | 2/1981 | Cerwin et al. . |
| 4,253,563 | 3/1981 | Komarnycky . |
| 4,284,194 | 8/1981 | Flatau . |
| 4,369,880 | 1/1983 | Giggey et al. . |
| 4,391,365 | 7/1983 | Batchelor . |
| 4,406,363 | 9/1983 | Aday . |
| 4,412,613 | 11/1983 | Kubas . |
| 4,412,614 | 11/1983 | Ivanov et al. . |
| 4,424,898 | 1/1984 | Thyen et al. . |
| 4,427,109 | 1/1984 | Roshdy . |
| 4,483,437 | 11/1984 | Cerwin et al. . |
| 4,496,045 | 1/1985 | Ferguson et al. . |
| 4,533,041 | 8/1985 | Aday et al. . |
| 4,549,649 | 10/1985 | Roshdy . |
| 4,555,016 | 11/1985 | Aday et al. . |
| 4,572,363 | 2/1986 | Alpern . |
| 4,573,575 | 3/1986 | Bergrath et al. . |
| 4,574,948 | 3/1986 | Huck et al. . |
| 4,574,957 | 3/1986 | Stead . |
| 4,615,435 | 10/1986 | Alpern et al. . |
| 4,699,271 | 10/1987 | Lincoln et al. . |
| 4,700,833 | 10/1987 | Smith . |
| 4,708,241 | 11/1987 | Black . |
| 4,813,537 | 3/1989 | Okuhara et al. . |
| 4,884,681 | 12/1989 | Roshdy et al. . |
| 4,896,767 | 1/1990 | Pinheiro . |
| 4,946,043 | 8/1990 | Roshdy et al. . |

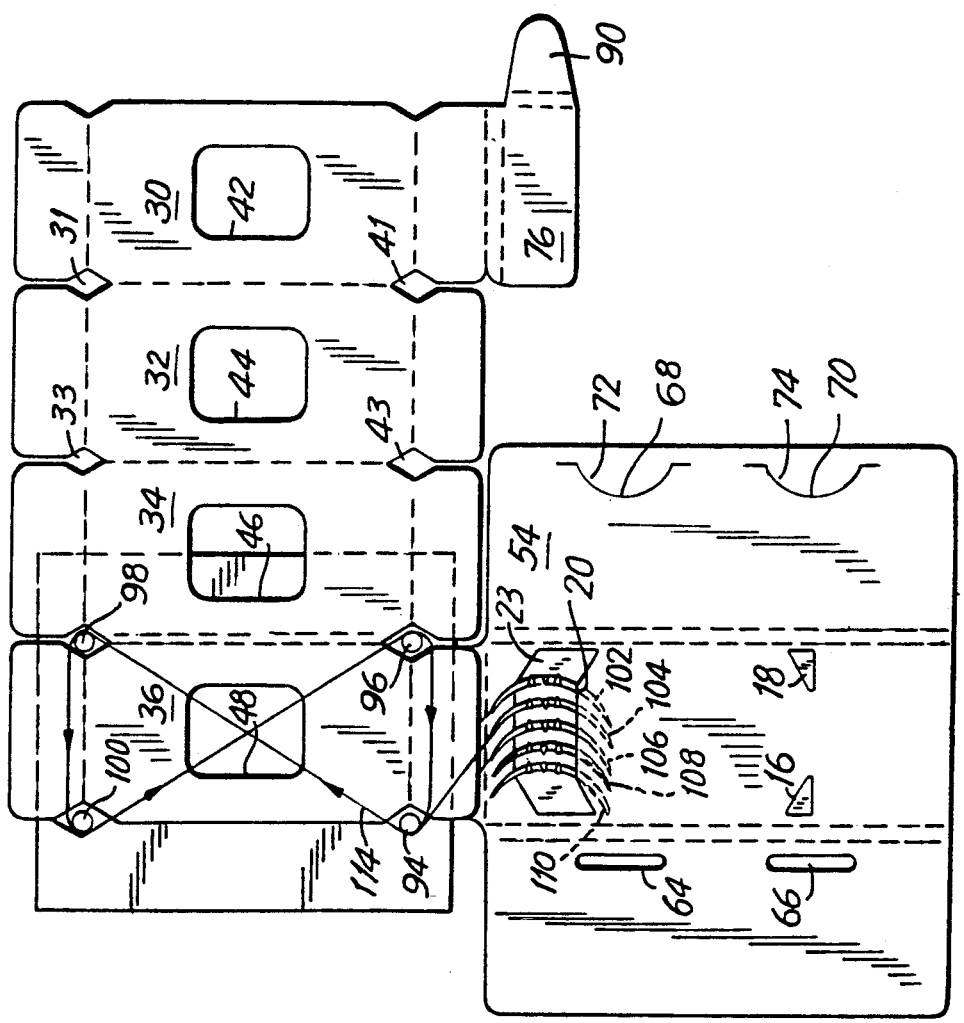

PACKAGE FOR MULTIPLE SUTURES

CROSS REFERENCE TO RELATED APPLICATION

This application is a continuation-in-part of copending U.S. patent application No. 07/629,114, filed Dec. 17, 1990, now abandoned.

BACKGROUND OF THE INVENTION

1. Field of the Invention

This invention relates to packages for multiple sutures whereby a plurality of panels define one individual compartment for the needles and a plurality of panels separate the flexible suture portions.

2. Description of the Prior Art

Packaging of surgical needles and sutures requires that the needles be secured properly to prevent displacement, as well as being simply and quickly removable from their packages for use by the surgeon. Jarring or displacement of such sharp needles will tend to dull their edges and reduce their effectiveness while increasing trauma to the patient during use.

Also it is desirable to package the needle/suture combinations in a manner where they are sufficiently separated for ready access to the user when they are needed. Moreover, the suture packages must be capable of receiving and holding sutures of various sizes while generally not affecting the quality, shape or strength of the suture in any way.

In general, a most significant objective in suture packaging is to store and maintain the relatively delicate ligatures in some form of spaced relation to each other so that access and removal of the suture may be readily available without adversely affecting the ligature or the needle as noted hereinabove. The present invention is directed to a suture package wherein a plurality of sutures may be stored in a single package while maintaining the individuality of each suture with respect to the others.

SUMMARY OF THE INVENTION

A suture package is provided which comprises a plurality of panel members foldably connected to each other and arranged to fold upon each other to form at least two individual suture compartments between pairs of adjacent panels. Needle holding means associated with at least one of the panel members to retain at least two suture needles in respective fixed positions whereby the needles are positioned in generally spaced relation and individual flexible suture portions are respectively positioned in the individual suture compartments formed by the remaining adjacent folded panels.

Preferably, the needle holding means is a planar resilient plastic insert member having portions cut out and lifted from the plane of the insert, with respective pluralities of the cut portions dimensioned and positioned thereon to retain the needles in the respective fixed positions.

The individual flexible portion of each suture is wound individually in a separate compartment formed by adjacent panels folded upon each other. Preferably the planar insert member is of resilient plastic material and is attached to one of the panel members.

The planar insert member is preferably retained in position on the one panel member by insertion of corner portions thereof into slits in the one panel member. The plastic member is preferably of generally rectangular configuration.

The one panel member contains at least four slits positioned and dimensioned for reception of corner portions of the plastic insert member therein to retain the plastic insert member thereon. Preferably the cut-out portions of the plastic insert member are "V" shaped cuts whereby material surrounded by the "V" shaped cuts is lifted out of the plane of said insert member to retain each needle on the insert member. Preferably, the cut-out portions of the plastic insert member are numbered and respectively positioned to retain a plurality of curved suture needles. Five needle/suture combinations are preferred.

The suture package includes at least two rows of generally rectangular panels connected to each other, at least one of the rows containing a plurality of rectangular panels connected to each other on the longer sides. The second row also includes a plurality of panels connected to each other on the longer sides. The two rows of panels are respectively connected to each other on the shorter sides of at least one panel in each row. At least one of the rows contains at least six panels and the other of the rows contains at least three panels. Certain of the panels define apertures generally centrally positioned to reduce the girth of the package. Each panel contains at least four notches, at least two notches on one panel facing the notches on the next adjacent panel, and dimensioned and positioned for reception of suture winding pins therethrough for winding the flexible suture portions therearound. At least one of the panels of the first row contains an end flap on a shorter side. The end flap has a generally tapered end portion and is adapted to be folded over one shorter side to protect the sutures. The second row of panels includes three panels, a first centrally positioned panel to support the plastic needle insert and two adjacent panels foldably connected to the first central panel. Each panel of the second row is generally rectangular and is connected to the next adjacent panel on a longer side.

Preferably the package is structured to receive at least five curved needles supported beneath the "V" shaped lift tabs of the insert panel, a first flexible suture portion being wound in a coiled configuration and positioned between a first panel and the next adjacent second panel, and a second flexible suture portion connected to the second needle being positioned in coiled configuration between the second panel and the next adjacent third panel. A third flexible suture portion is connected to the third needle and is positioned in coiled configuration between the third panel and the next adjacent end panel and a fourth flexible suture portion is positioned in coiled configuration between the end panel and a fourth panel connected to the third panel. A fifth flexible suture portion is positioned in coiled configuration between the fourth panel and a fifth panel connected to the fourth panel.

In one embodiment the suture package comprises a first row of six generally rectangular shaped panels connected to each other by fold lines along the longer sides, a second row of three generally rectangular shaped panels connected to each other by fold lines along the longer sides, the central panel of the second row being connected to a second panel of the first row by a fold line along the shorter sides thereof. The central panel of the second row defines a plurality of cuts for reception of a generally rectangular needle retainer panel. A flexible plastic needle retainer panel is attached to the central panel of the second row by insertion of the corner portions into the cuts in the panel having a plurality of "V" shaped cut-outs adapted to be defined out of the plane of the insert for retaining five curved suture needles thereon. The panels are respectively folded in a manner to form compartments between adjacent panels, each compartment containing at least one flexible suture portion therein in a wound configuration. The panels are finally folded to form a generally rectangular suture package. Each flexible suture portion is wound in the respective compartment in a figure "8" configuration.

In another embodiment, each panel contains a rectangular aperture to reduce the girth of the package, whereas in still another embodiment a plurality of generally elongated tapered apertures are provided to facilitate loading the package with needled sutures on a suture winding fixture and to provide access for fluids to the compartment.

In still another embodiment certain of the panels are fabricated of less material by dimensioning such panels approximately one half of the length of the other panels. In each embodiment a needle protective end flap may be foldably attached to one of the panels in either row to be folded over the suture/needle connection portion of the needle to cover and to protect the needle.

Still another embodiment of the suture package comprises a plurality of panel members foldably connected to each other and arranged to fold upon each other to form a suture compartment between pairs of adjacent panels, at least two panel members having a generally central portion cut away to reduce the girth of the combined sutures and panels. A generally planar insert member has portions cut out and lifted from the plane of the insert, respective pluralities of said cut portions being dimensioned and positioned to engage respective portions of at least two suture needles positioned thereon to retain said needles in respective fixed position within the package whereby said needles are positioned in generally spaced relation in one compartment and individual flexible suture portions are respectively positioned in individual compartments formed by the remaining adjacent folded panels.

The package is preferably formed from a sheet of Tyvek brand 5 to 10 point polyolefin spun fibers which provides sufficient slip to smoothly withdraw the suture strands. Alternatively, surgical paper such as uncoated 5 point Kraft paper may be used.

BRIEF DESCRIPTION OF THE DRAWINGS

Preferred embodiments of the invention are described hereinbelow with reference to the drawings wherein:

FIG. 4 is a view similar to FIG. 2A, with the first panel folded over the second suture being wound about suture winding pines into the second compartment formed between the panels;

DESCRIPTION OF THE PREFERRED EMBODIMENTS

Figure 1A:
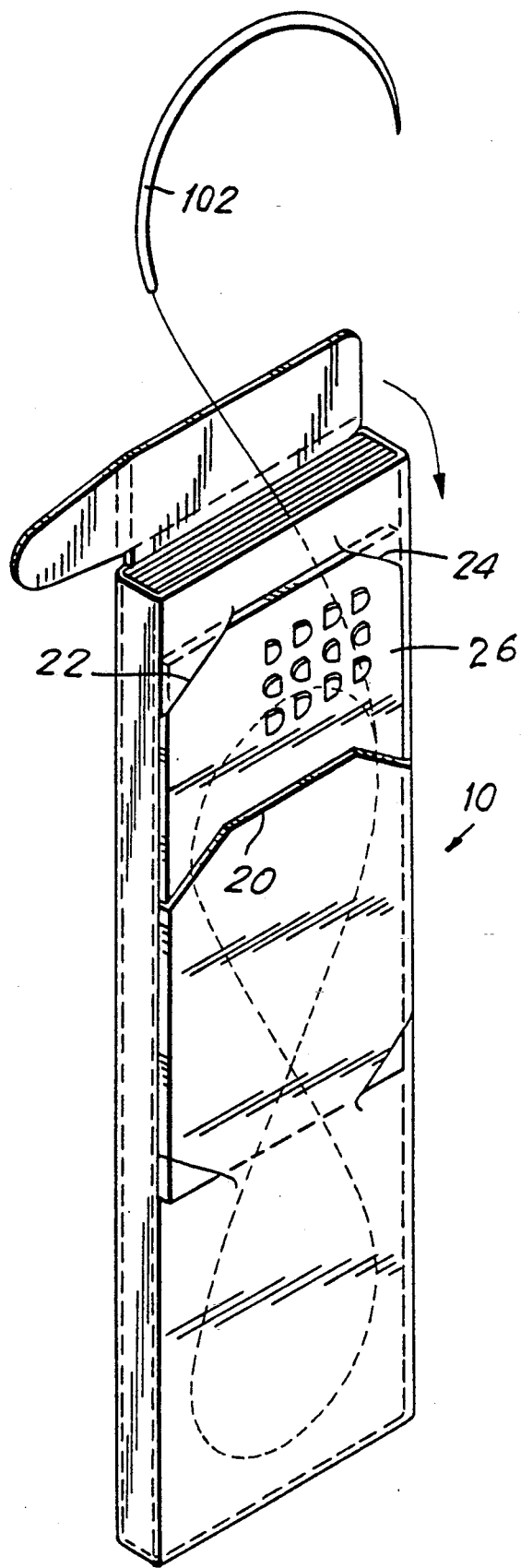
FIG. 1A is a perspective view from the left side, of a package for multiple sutures constructed according to the present invention with all but one suture removed and illustrating removal of the last suture.
Figure 1B:
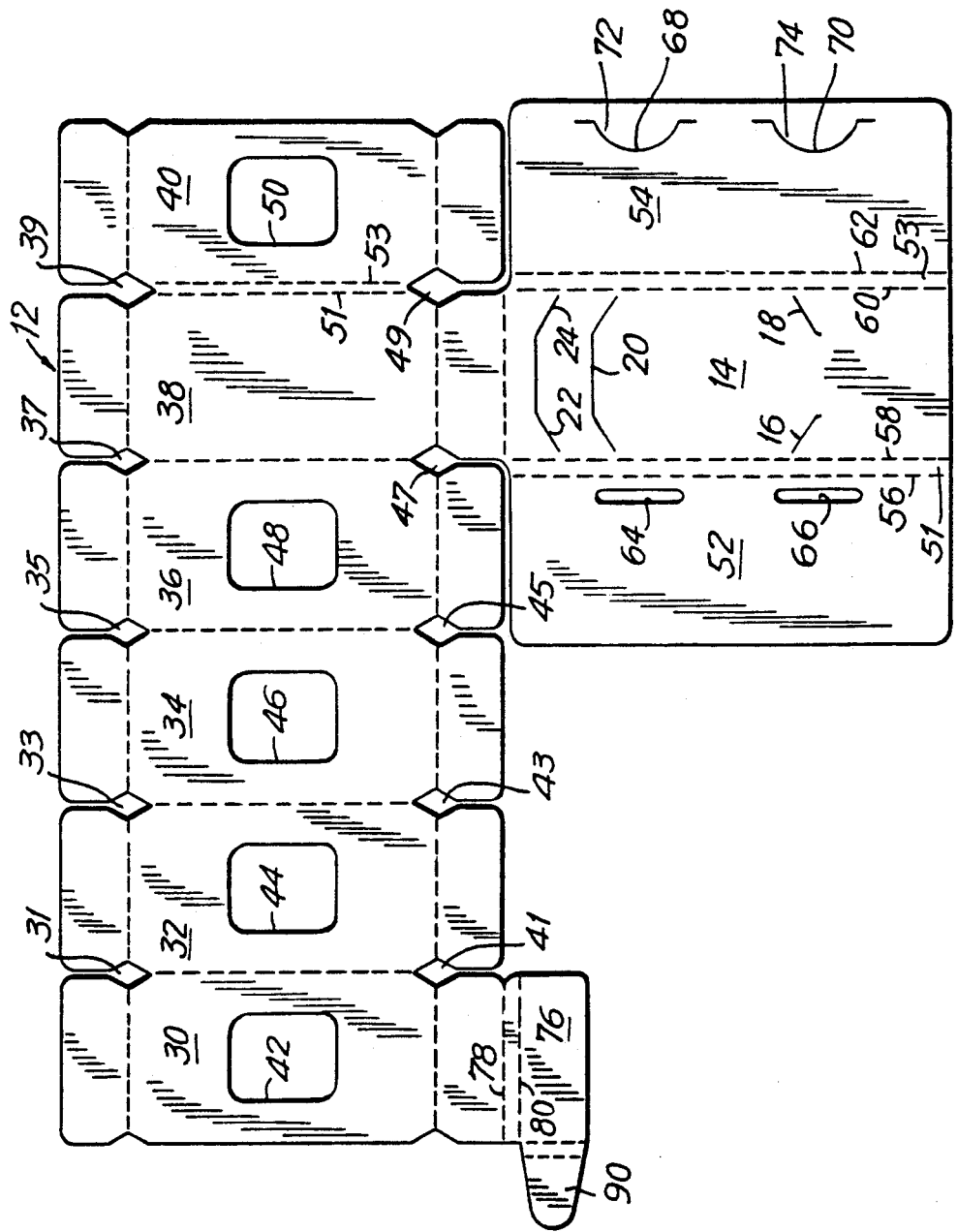
FIG. 1B is a plan view of a blank sheet constructed according to the invention defining a plurality of panel members foldably connected to each other.

Referring initially to FIG. 1A a five needle suture package 10 constructed according to the present invention is illustrated. The package is shown with all sutures except one removed for convenience of illustration. The last suture is shown partially removed from the package. FIG. 1B is a plan view of a blank sheet constructed according to the invention and defining a plurality of panel members foldably connected to each other to form individual suture compartments. When folded and provided with a needle holder insert panel as will be described, the suture package of FIG. 1B will appear as shown in FIG. 1A.

Figure 2A:
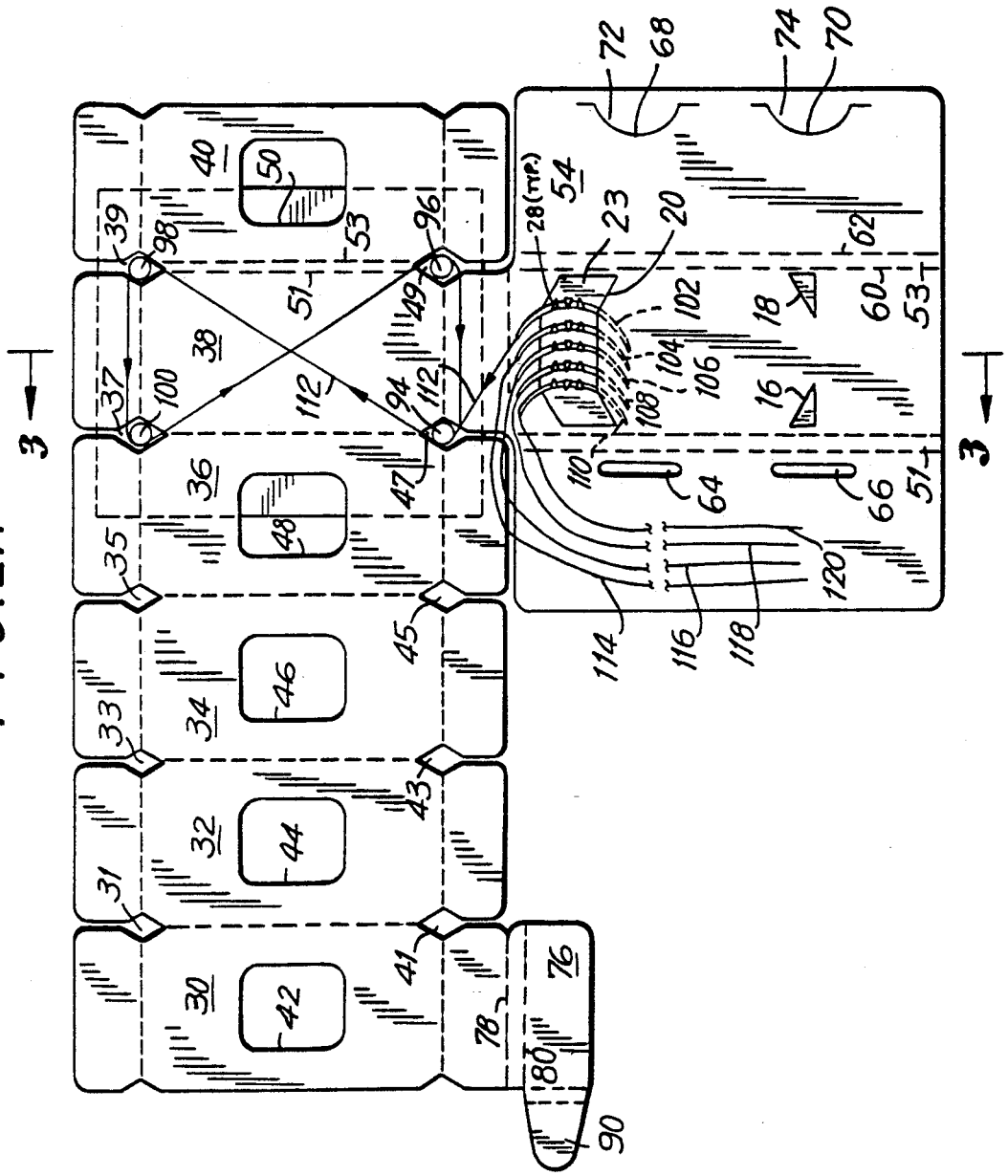
FIG. 2A is a view similar to FIG. 1B with a needle retaining planar insert member with five needles in position and illustrating the procedure to wind the first of the sutures about winding pins of a suture wrapping fixture.
Figure 2B:
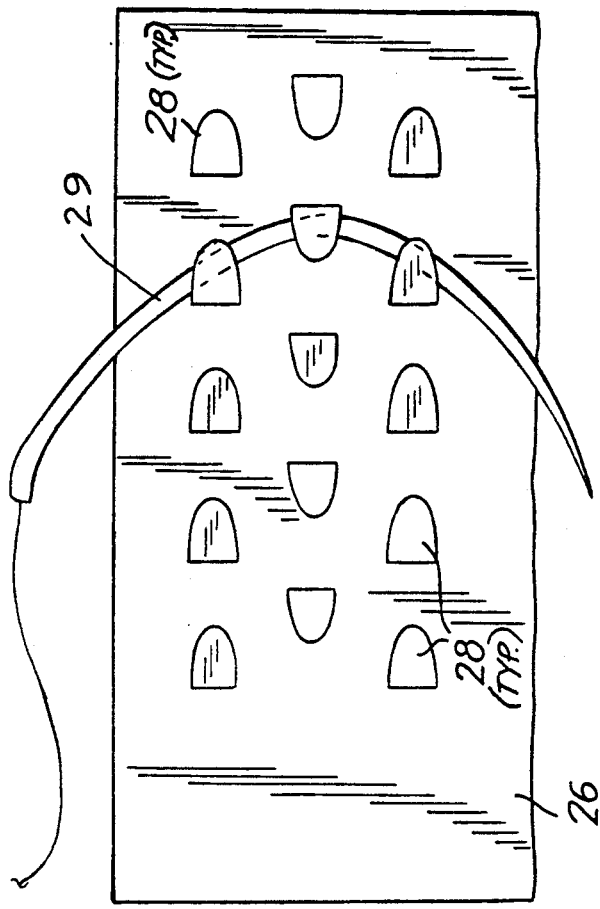
FIG. 2B is an enlarged fragmentary view illustrating a portion of a needle retaining planar insert member constructed according to the invention, with one exemplary needle retained in position thereon.

Referring once again to FIG. 1B, the blank sheet 12 is illustrated including panel 14 having cuts 16, 18, 20, 22, and 24 which are dimensioned, oriented and positioned to receive a resilient plastic needle retainer sheet 26 shown in FIGS. 1A and 2B. The needle retainer sheet 26 is a planar sheet of plastic material having generally "V" shaped cuts 24 which define tabs which respectively alternate in direction and which are conveniently positioned to be lifted so as to receive and retain a plurality of curved suture needles in position as shown in FIG. 2B by exemplary needle 28. The plastic insert sheet 26 is rectangular in shape and is inserted into position in panel 14 such that the lower cuts 16, 18, retain the lower corners and the upper cuts 22, 24 retain the upper corners. The upper mid-portion of the sheet extends through cut 20 such that the upper portions of the sheet and needles are exposed as shown in FIGS. 1A and 2A.

Referring once again to FIG. 1B, the blank sheet 12 includes separate and individual panels connected to each other as shown. An upper row of panels 30, 32, 34, 36, 38 and 40 are provided with individual respective cut out portions 42, 44, 46, 48 and 50 to reduce the girth of the package. In addition, with the rear panel opened, the sutures may be viewed through the cut out portions as will be appreciated below. Panels 52 and 54—being the rear panels of suture package 10—do not include a cut out portion and therefore provide cover protection for the sutures.

Each panel 30, 32, 34, 36 and 38 is connected to the next adjacent panel by a single fold line, with front panel 14 being connected to rear panels 52 and 54 by double fold lines 56, 58, 60 and 62 to accommodate the thickness of the package and sutures. Intermediate encompassing panel 40 is also connected to the next adjacent panel 38 by double fold lines 51 and 53 to accommodate the girth of the first three panels—i.e. 38, 36, and 34 as will be seen in the description which follows.

Referring further to FIG. 1B, slotted cut outs 64, 66 are provided in panel 52 and correspondingly positioned arcuate cuts 68 and 70 are provided in panel 54. These cut-outs and cuts are intended to close the package.

Referring once again to FIG. 1B, the upper row of panels includes a foldable end flap 76 connected to panel 30 by double fold line 78, 80 to accommodate the thickness of the package. This end flap includes a generally tapered extension 90 which functions to lock the package in the final folded condition as will be described. Each panel 30, 32, 34, 36, 38 and 40 includes "V" shaped cuts at the top and bottom side portions to form, with the next adjacent panel, diamond shaped openings 31, 33, 35, 37, 39, 41, 43, 45, 47, 49 to accommodate winding the suture as will be described.

Figure 3:
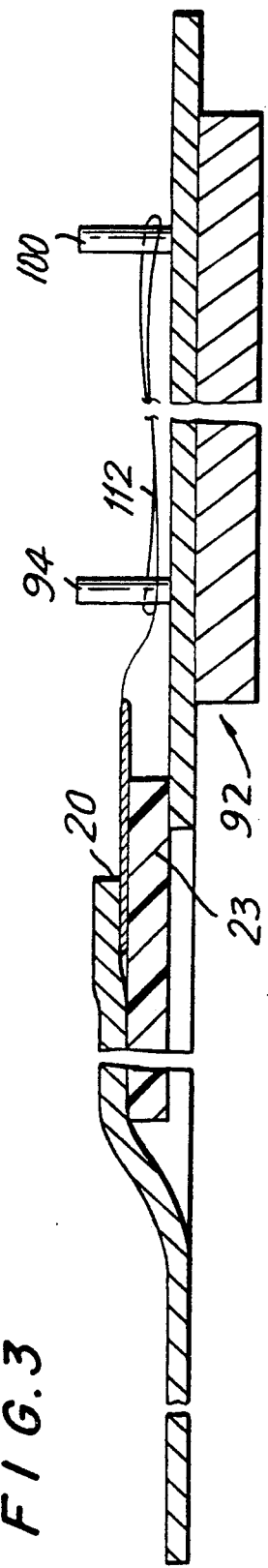
FIG. 3 is a cross-sectional view taken along lines 3—3 of FIG. 2A illustrating the needle and the corresponding procedure to wind the suture about suture winding pins of a suture winding apparatus.

Referring now to FIG. 3, a cross-sectional view of a suture wrapping fixture 92 is illustrated for packaging sutures in the package of the present invention. The wrapping fixture 92 includes upstanding pins, 94, 96, 98 and 100, which are dimensioned, configured and spaced for entry into the diamond shaped openings 31, 33, 35, 37, 39, 41, 43, 45, 47 and 49 formed by the adjacent "V" cuts on the sides of the panels as shown in FIGS. 2A and 3. The wrapping fixture is configured to receive the flat sheet of panels for wrapping sutures as set forth hereinbelow.

The flat sheet 12 of multiple panels as shown is preferably cut from a suitable package paper which is rigid yet flexible, and which is of sufficient thickness to separate and isolate the individual sutures from each other. It has been found that a paper panel material approximately 0.005 inch thickness is suitable and desirable. The flat sheet is preferably formed from a spun bonded polyolefin, free of any impurities which would adversely affect the sutures. A preferred material is 5 point to 10 point Tyvek brand spun bonded polyolefin sheet marketed by DuPont DeNemours, Wilmington, Del. Tyvek brand sheet has lower frictional properties for example, than conventional paper materials and thus permits ease of removal of the needles. Other preferred materials include paper or paperboard material such as 5 point uncoated surgical Kraft paper, also free of impurities which would adversely affect the sutures. Such a preferred paper material is uncoated surgical Kraft paper, about 5 point in weight.

As shown in FIG. 2A in conjunction with FIG. 2B, a plastic needle holder sheet 23 is inserted into cut 20 in panel 14 with upper corners inserted beneath upper cuts 22, 24 and the lower corners inserted beneath lower cuts 16, 18. Individual suture needles 102, 104, 106, 108 and 110 are positioned beneath respective tapered lift tabs 28 to retain the needles in position as shown in FIG. 2A, with each tab alternately facing the next adjacent tab. The points of the needles face downwardly and are protected by the lower portion of package material defined by cut 20. The ligatures of the sutures are temporarily gathered and set aside as shown in FIG. 2A except for the first ligature 112 which is connected to needle 102. This ligature 112 is wound into a figure "8" pattern around pins 94, 96, 98, 100 as shown.

Figure 5:
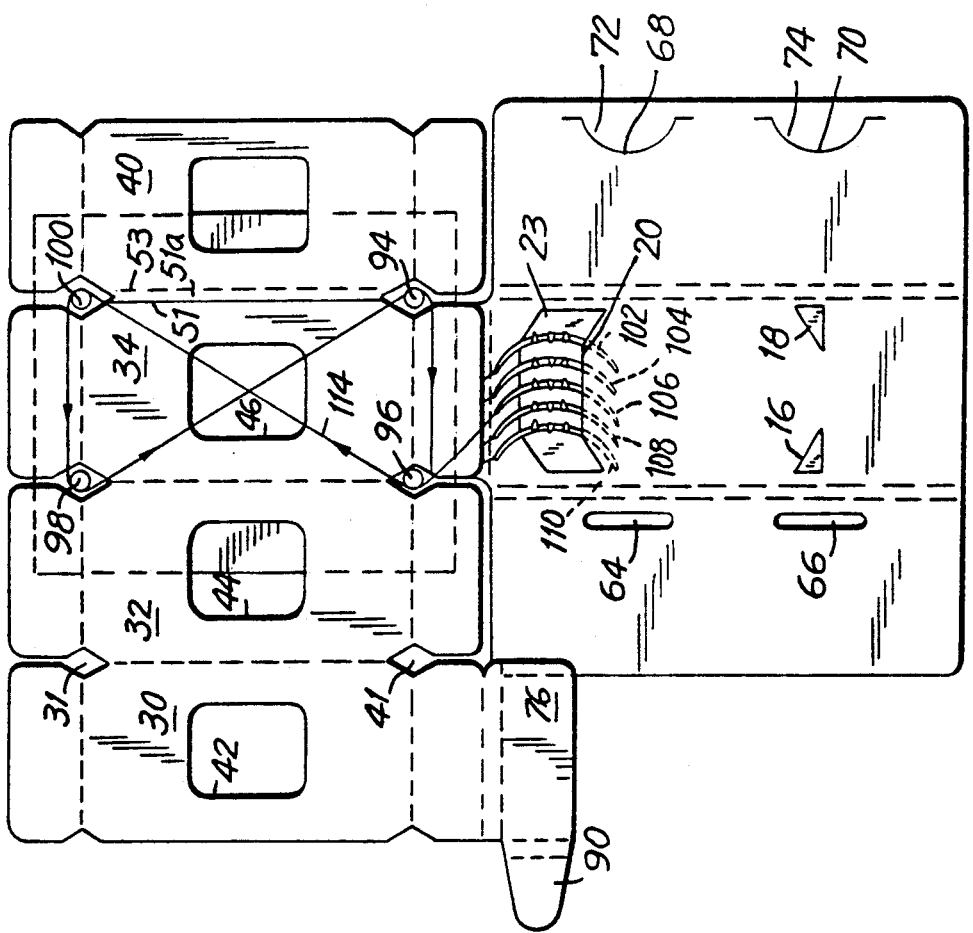
FIG. 5 is a view similar to FIG. 4 showing the third panel folded over the previously folded panels and illustrating the procedure for winding the third suture about winding pins into its respective compartment.

Referring further to FIG. 2A, ligature 112 is alternately and continuously wrapped about pins 94, 96, 98, 100 as shown until completely wound about the pins. Thereafter, panel 36 (with the remaining panels 34, 32, 30) is folded to the right over panel 38 and ligature 112 is shown in FIG. 4, such that ligature 114 connected to needle 104 may be alternately and continuously wrapped about pins 94, 96, 98, 100 until completely wound into a figure "8" pattern. Next, panel 34 (and the remaining panels) is folded to the left over panel 36 as shown in FIG. 5 whereby ligature 114 connected to needle 106 may be alternately and continuously wrapped around pins 94, 96, 98 and 100 to form a figure "8" pattern as shown in FIG. 5.

Figure 7:
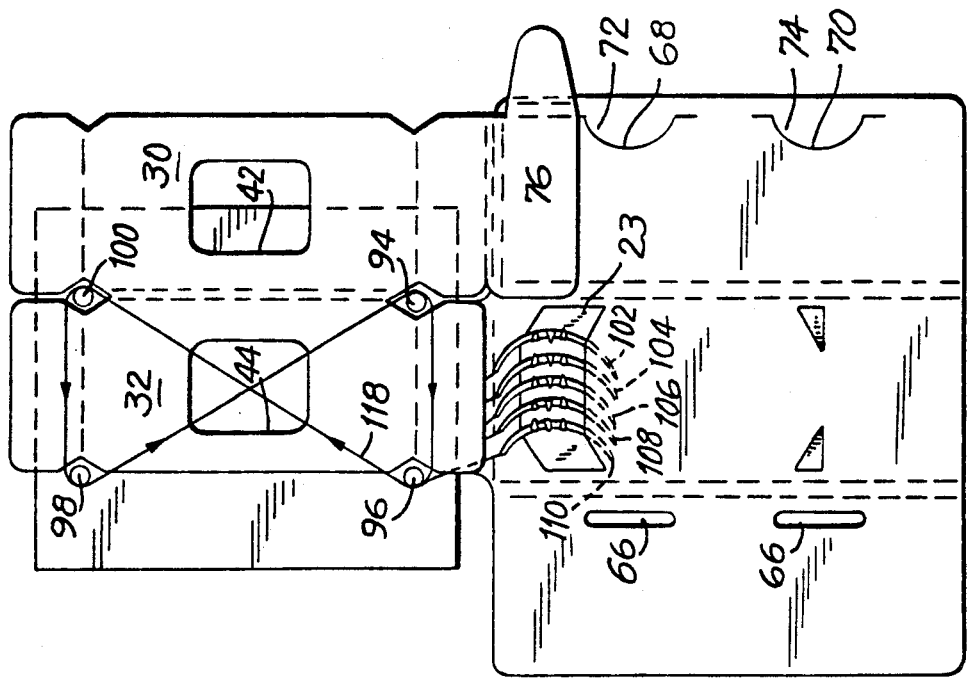
FIG. 7 is a view similar to FIG. 6 with the fourth panel folded over the previously folded panels and illustrating the procedure for winding the fifth suture into its respective compartment.
Figure 8:
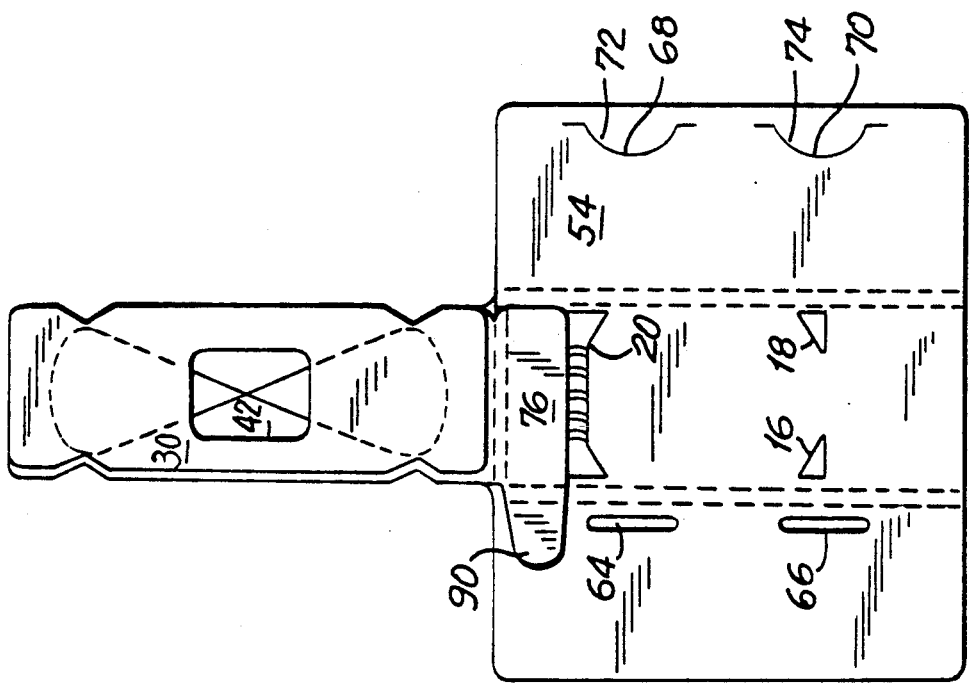
FIG. 8 is a view similar to FIG. 7 with the fifth and last panel folded over the previously folded panels into its final folded position.
Figure 6:
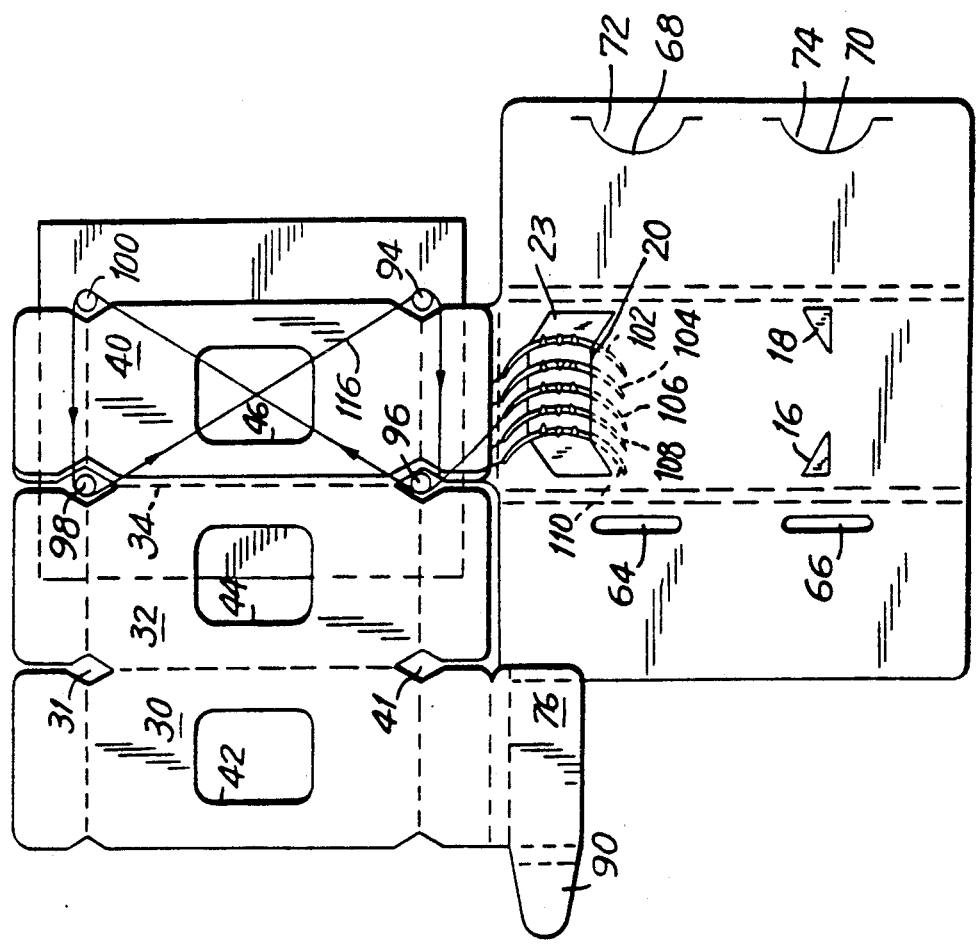
FIG. 6 is a view similar to FIG. 5 with the side panel folded over the previously folded panels and illustrating the procedure for winding the fourth suture about winding pines into its respective compartment.

Referring now to FIG. 6, end panel 40 is then folded to the left over panel 34 and ligature 14 such that the relatively narrow side panel 51a defined by the double fold lines 51, 53 may encompass the combined side edges of the previously folded panels 38, 36 and 34. After folding panel 40 as shown in FIG. 6, the ligature 116 connected to needle 106 is wrapped about pins 94, 96, 98, 100 as shown until complete wound. Thereafter, panel 32 is folded over the ligature 116 as shown in FIG. 7 whereby ligature 118 attached to needle 108 may be wound in a Fig. "8" pattern about pins 94, 96, 98, 100 until completely wound. Finally, remaining panel 30 is folded over the last ligature as shown in FIG. 8.

Figure 9:
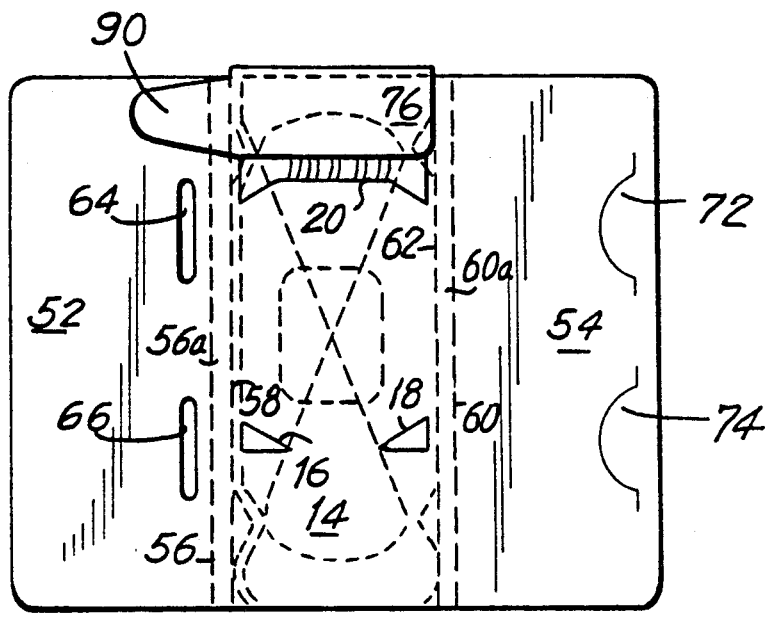
FIG. 9 is a view illustrating the combined panels and sutures folded in position behind the face panel and illustrating the needle butt end cover tab in the last folded position.
Figure 12:
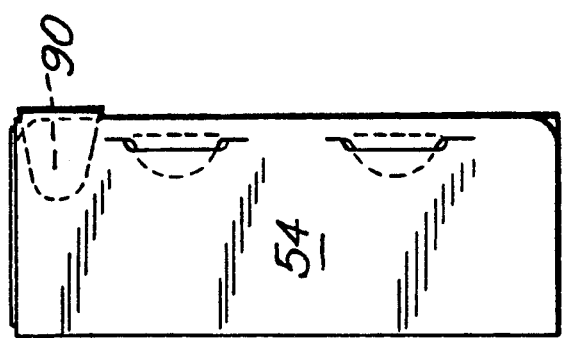
FIG. 12 is a rear view of the folded suture package of FIG. 11 illustrating the locking tab feature which retains the package in its final folded position.
Figure 10:
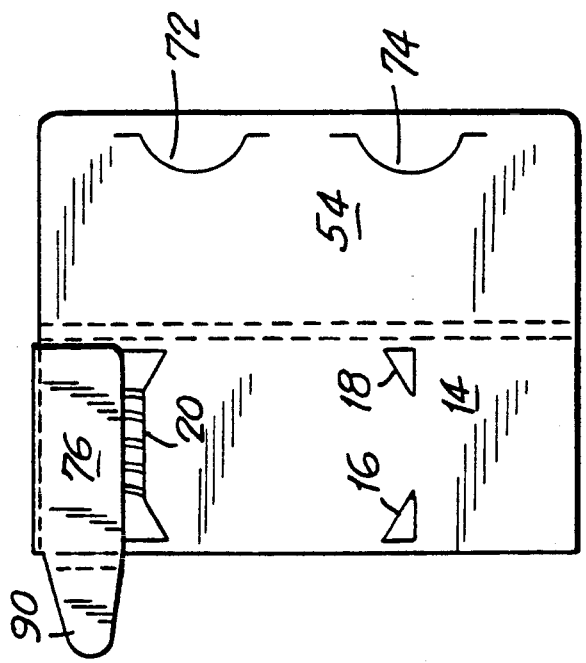
FIG. 10 is a frontal view of the package for multiple sutures with the left hand panel folded behind the package.

Referring now to FIG. 9, the suture package is illustrated with the entire folded suture panels and ligatures folded downwardly behind the front panel 14. Thereafter, panel 52 is folded along the double fold lines 56, 58 such that the relatively narrow edge panel 56a encompasses all of the folded panels along the left side. Then side panel 54 is similarly folded along the double fold lines 60, 62 as shown such that the narrow edge side panel 60a encompasses the previously folded panels along the right side. Arcuate tabs 72, 74 of rear panel 54 are then inserted into slots 64, 66 of rear panel 52 to retain the panel in a closed condition. Rear panel 54 also serves to retain the tapered end flap 90 of end tab 76 in position as shown in FIG. 12 which is a rear view of the suture package. FIG. 10 illustrates a front view of the package prior to folding the final rear panel 30 into position.

Figure 13:
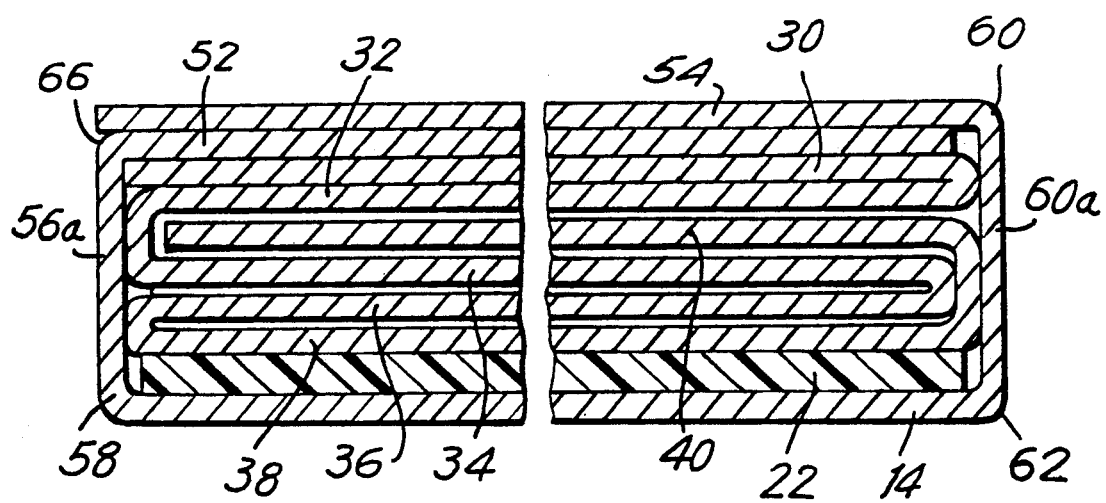
FIG. 13 is an enlarged cross-sectional view taken along lines 13—13 of FIG. 11 illustrating the individual panels which form the compartments for the sutures (not shown in this Fig.)
Figure 11:
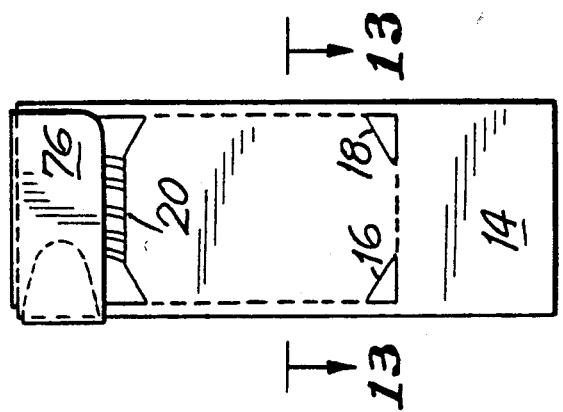
FIG. 11 is a frontal view of the completed suture package of FIG. 10 with the right hand - and final - panel folded in position at the rear of the package.

Referring now to FIG. 13 there is shown a cross-section of the suture package taken along lines 13—13 of FIG. 11, illustrating the panel folding sequence described above. For example, from panel 14 and plastic insert 22 are shown in cross section. Panels 38, 36, 34, 40 are shown in their folding sequence as described hereinabove. Rear panels 52, 54 are also illustrated.

Figure 14:
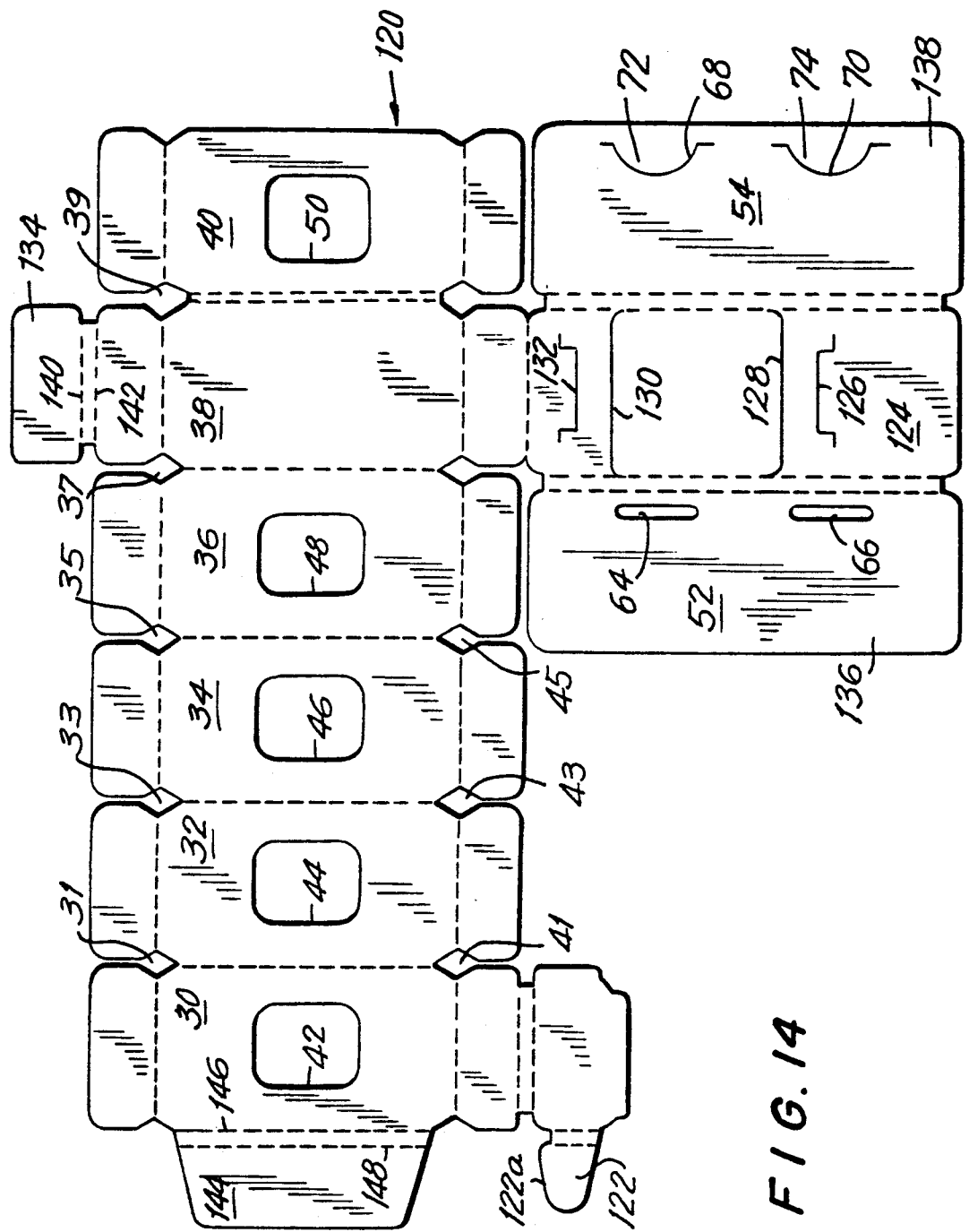
FIG. 14 is a plan view of an alternative embodiment of the blank sheet shown in FIG. 1B.

Referring now to FIG. 14, there is illustrated an alternative embodiment of the blank sheet of panels 12 shown in FIG. 1B. In the embodiment 120 shown in FIG. 14, the panels and tabs are shaped to provide additional relief at the fold lines. For example, tab 90 of blank sheet 12 shown in FIG. 1B is defined by straight tapered sides, whereas corresponding tab 122 in the blank sheet shown in FIG. 14 includes arcuately configured side 122a to provide more convenient folds. Further, for example, the face panel 124 includes cuts 126, 128, 130 and 132 as shown to provide an alternative means for retaining the plastic needle retainer insert. An additional side panel flap 144 is provided and connected by double fold lines 146, 148 to the side edge of panel 30. Flap 144 is dimensioned and adapted to assist the operator during removal of the loaded package from the winding fixture, and is folded over and pressed against the loaded suture panels to hold the sutures in place while the loaded pins are withdrawn. An extra end flap 134 is also provided and connected by double fold lines 140, 142, as shown, for the purpose of providing closure of the bottom edge of the package prior to folding the last and the penultimate panels 136 and 138. This feature provides additional protection for the sutures. Tab 122, which corresponds to tab 90 of blank sheet 12 shown in FIG. 1B, includes arcuately configured side 122a which provides additional relief at the fold line and for a more convenient fold. Face panel 124 includes cuts 126, 128, 130 and 132 as shown to provide an alternate means for retaining the plastic needle retainer insert. In other respects the blank sheet of folding panels shown in FIG. 14 is essentially the same as the first described embodiment.

Figure 15:
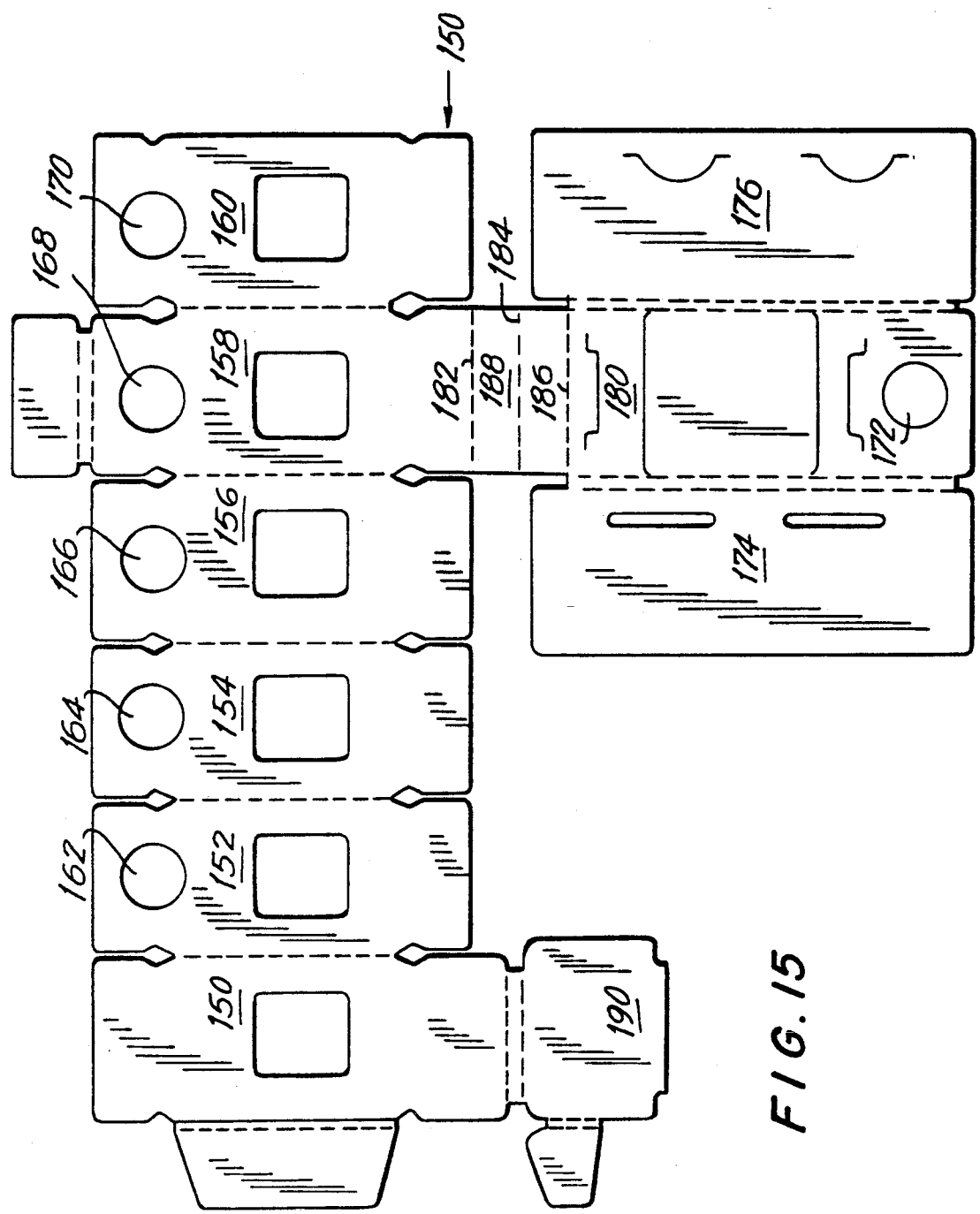
FIG. 15 is a plan view of another alternative embodiment of the blank sheet shown in FIG. 1B.
Figure 16:
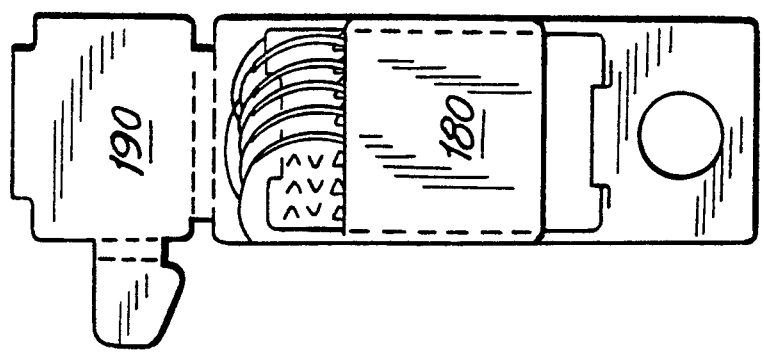
FIG. 16 is a frontal view of the embodiment of FIG. 15 in a partially folded condition with the end tab in the unfolded condition.

Referring now to FIG. 15, there is illustrated another embodiment of the present invention. In this embodiment, panel 180 and the upper row of panels 152, 154, 156, 158 and 160 are provided with individual respective cut-out circular apertures 162, 164, 166, 168 and 170 to allow packing fluid, i.e., isopropyl alcohol, to be added to the package when the package is in the folded condition. Panel 150—being the rear most panel of the upper row of panels when the package is in the folded condition—is not provided with a circular aperture to prevent the packing fluid from escaping the suture retaining area of the package. The top edges of panels 152, 154, 156 and 160 have been lowered as shown as compared to the top edges of the embodiments of FIGS. 1B and 14. Such lowering provides distinct advantages in terms of suture-needle visibility and decreased bending stress on the suture. As best illustrated by FIG. 16, the upper portion of the package is open and unobstructed thereby providing greater access to the needle and suture. The top of the package also provides a greater area for the suture to curve away from the needle, resulting in less stress on the suture and needle attachment while also providing a neater appearance.

Figure 17:
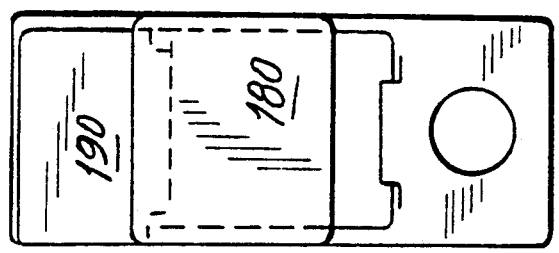
FIG. 17 is a frontal view of the embodiment of FIG. 15 in the fully folded condition.

Referring again to FIG. 15, panel 180 is adjoined to panel 158 of the first row of panels by intermediate panel 188. Intermediate panel 188 is folded over upon itself along fold line 184 when folding the upper row of panels against the lower row of panels. This folded arrangement of panel 188 provides a double layer of panels between panel 180 and the upper row of panels which in effect spaces panel 180 away from the upper row of panels to provide additional clearance between the needle holding panel and the loaded suture portion of the package. Such clearance aids in providing needle visibility and access during operating procedures and also reduces the bending stress on the suture portion neighboring the needle. The upper portion of the package when folded is open and unobstructed, thereby providing good visibility and access to the needles and sutures. Another feature of this embodiment is the length of end tab 190 which is extended to completely cover the needles when the suture package is in the final folded condition as shown in FIG. 17. FIG. 16 shows the package prior to folding end tab 190 over in the final position.

Figure 18:
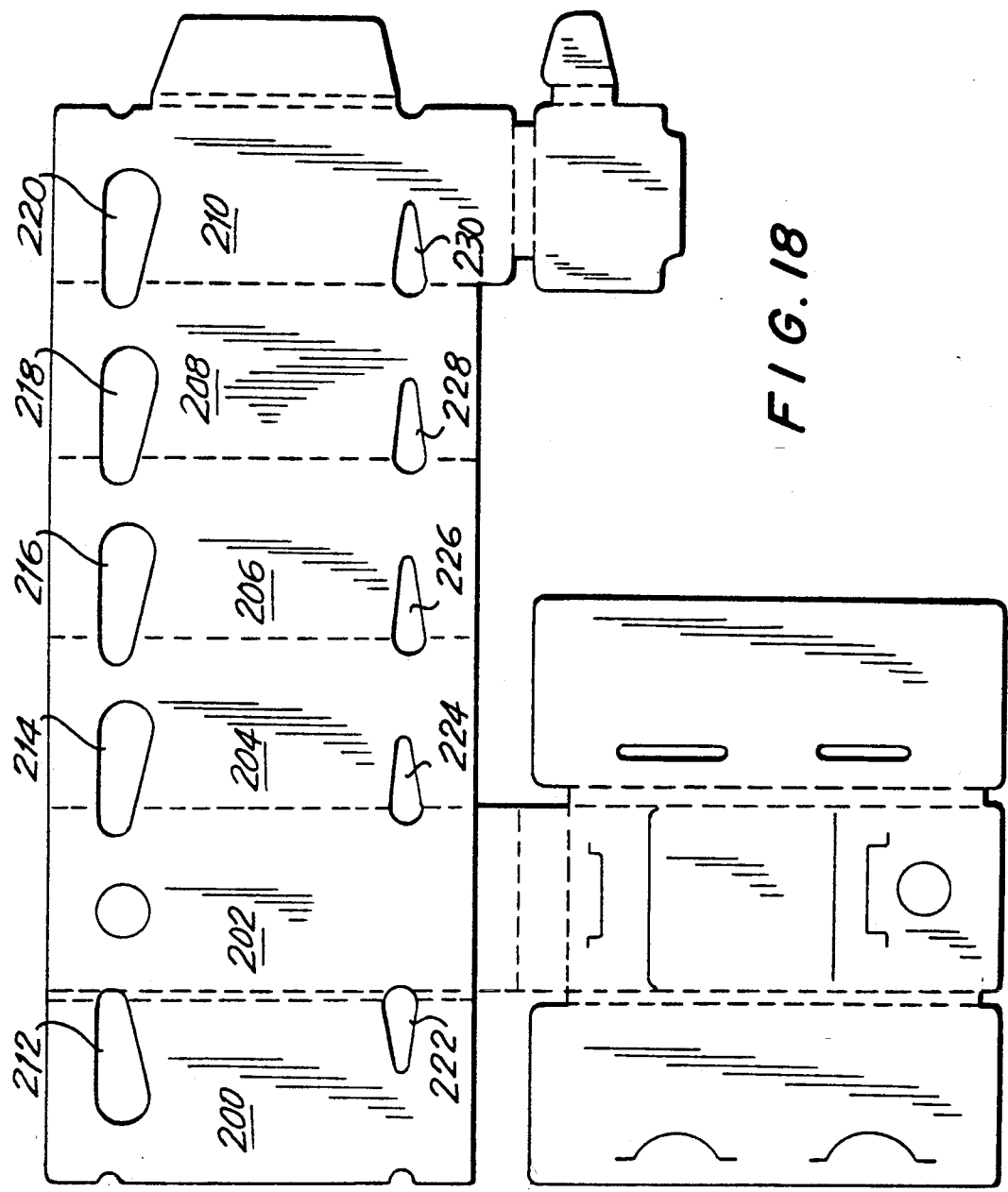
FIG. 18 is a plan view of another alternative embodiment of the blank sheet shown in FIG. 1B.
Figure 19:
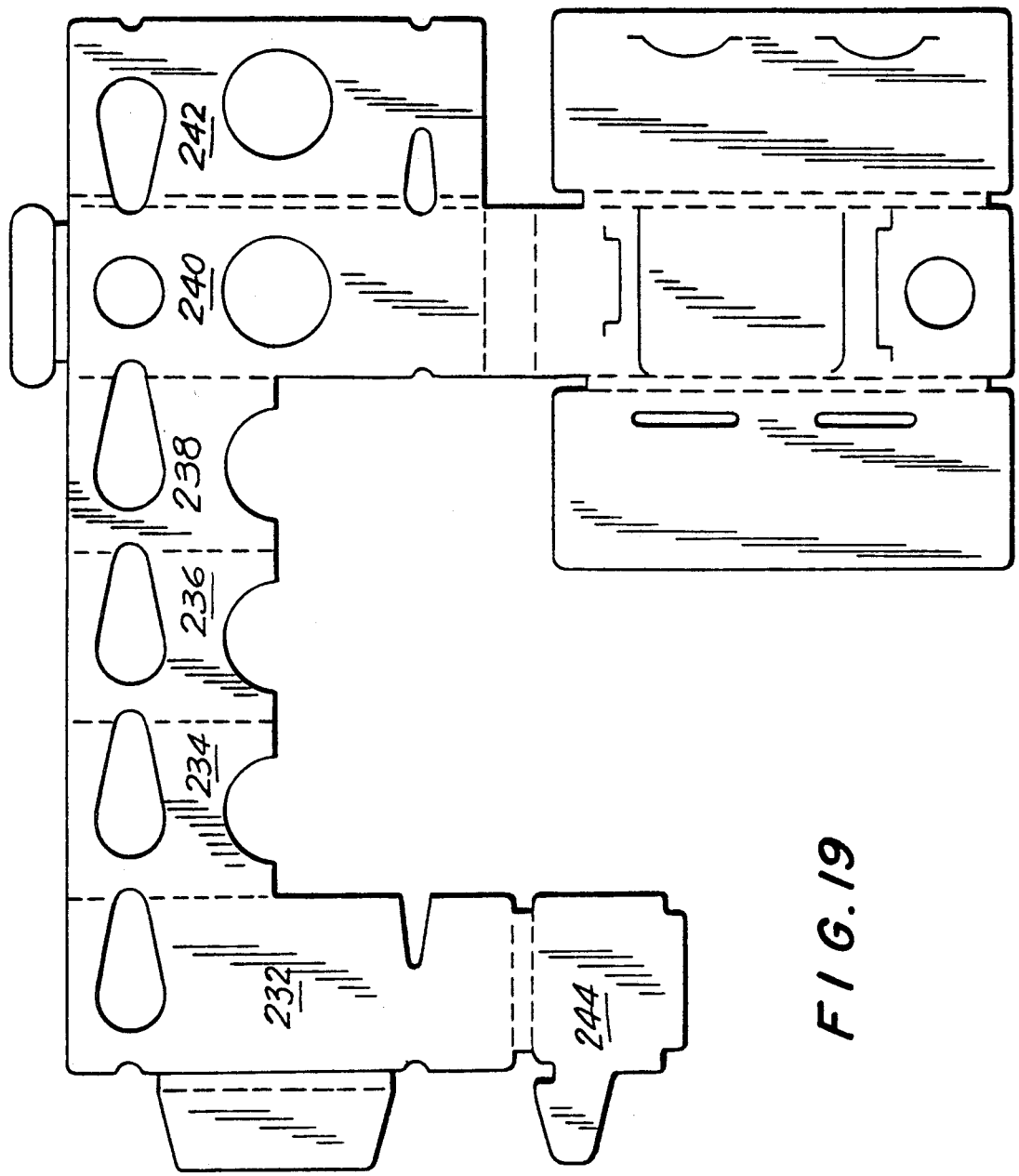
FIG. 19 is a plan view of still another alternative embodiment of the blank sheet shown in FIG. 1B.
Figure 20:
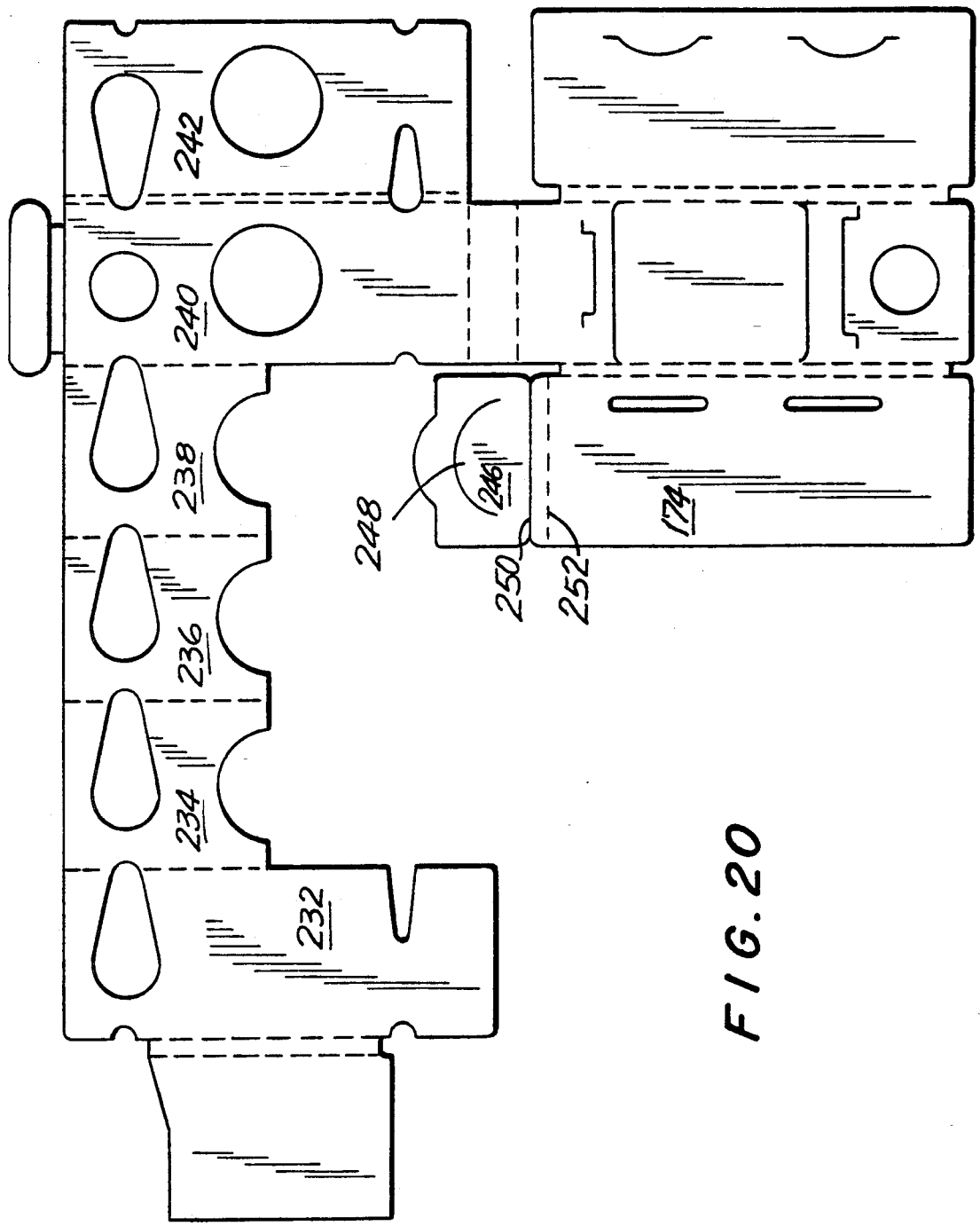
FIG. 20 is a plan view of still another alternative embodiment of the blank sheet shown in FIG. 1B.

Alternative embodiments will now be described as shown in FIGS. 18-20. In connection with these embodiments the folding sequence is the same as described with respect to the previous embodiments and are therefore not repeated herein for the sake of brevity.

Referring now to FIG. 18, another embodiment of the present invention is described. In this embodiment, panels 200, 204, 206, 208 and 210 are each provided with two tapered oval apertures. Similar to the circular apertures of the embodiment of FIG. 15, the tapered oval apertures 212, 214, 216, 218, 220, 222, 224, 226, 228 and 230 serve as a means to permit packing fluid, i.e., isopropyl alcohol, to be added to the package when the package is in the folded condition. The apertures also are positioned and configured to receive the suture winding pins for suture wrapping, thus replacing the diamond shaped openings 31, 33, 35, 37, 39, 41, 43, 45, 47 and 49 of the embodiment of FIG. 1B.

The tapered oval apertures in FIG. 18 provide a distinct advantage during suture winding and loading. Specifically, the length of the tapered oval apertures facilitates folding of the panels on the winding fixture by providing a clearance such that each panel can be folded over without engagement of the portion of the panel adjacent to the suture winding pin with the winding pin. For example, during suture winding of panel 202, the suture winding pins project upwardly through the plane of the panel and through the tapered apertures. When the suture is completely wound on the panel, panel 204 is folded onto panel 202. The length of apertures 214 and 224 permit the portions of panel 204 neighboring the winding pins to clear the tops of the suture winding pins and fold onto panel 202 without interference of the pins with the panel during the folding process. As panel 204 is folded over panel 202, apertures 216 and 226 align with portions of apertures 212 and 222 and receive the winding pins on the opposite side of panel 202. Similar alignment of the winding pins and the tapered apertures occurs during subsequent folding steps without interference therebetween.

Referring now to FIG. 19, another embodiment of the present invention is described. In this embodiment, half panels 234, 236 and 238 are provided to reduce the overall bulk of the suture package when the package is in the completely folded condition. The half panels also prevent the loaded sutures from catching on the packing fluid aperture.

Referring now to FIG. 20, another embodiment of the present invention is illustrated. In this embodiment the end closure tab is moved from its original location wherein it is attached to the first panel on the first row of panels (compare panel 244 of FIG. 19) to an alternative location wherein it is configured as shown at 246 and attached to panel 174 of the second row of panels by double fold lines 250, 252 to allow for the thickness of the package when folded over in the final position. This feature ensures that upon the lifting of end tab 248 to expose the loaded needles, the lifting motion of the end tab—which is now secured to the second row of panels—will prevent inadvertent removal of the interior first row of panels from the closed suture package which might otherwise occur as a result of the reduced dimensions of interior panels 234, 236, 238. Another feature of this embodiment is that the length of flap 246 is sufficiently extended to assist the operator during removal of the loaded package from the winding fixture, and to hold the sutures in place while the loaded pins are withdrawn.

The above embodiments have been shown and described as examples of the present invention, and other modifications and embodiments are contemplated within the spirit of scope of the present invention as defined by the following claims.

We claim:

1. A suture package storing at least two flexible suture portions, each having at least one needle attached thereto, which comprises:
   a) a plurality of panel members foldably connected to each other and arranged to fold upon each other to form at least two individual suture compartments between pairs of adjacent panels; and
   b) a needle holding insert member attached to one of said panel members and retaining all such suture needles in respective fixed spaced positions wherein all such needles are positioned in generally spaced relation on said insert member and the individual flexible suture portions are respectively positioned in said individual suture compartments formed by the remaining adjacent folded panels.

2. The suture package according to claim 1 wherein each said individual flexible suture portion is individually wound in a separate suture compartment formed by adjacent panels folded upon each other.

3. A suture package for storing at least two flexible suture portions, each having at least one suture needle attached thereto, which comprises:
   a) a plurality of panel members foldably connected to each other and arranged to fold upon each other to form at least two individual suture compartments between pairs of adjacent panels; and
   b) a substantially planar insert member attached to one panel member and having portions cut and lifted from the plane of the insert member, respective pluralities of said cut portions being dimensioned and positioned to engage respective portions of said suture needles to retain said needles in respective fixed positions whereby said needles are positioned in generally spaced relation and individual flexible suture portions are respectively positioned in individual compartments formed by the remaining adjacent folded panels.

4. The suture package according to claim 3 wherein said planar insert member is of resilient material.

5. The suture package according to claim 4 wherein said resilient material is plastic.

6. The suture package according to claim 4 wherein said cut-out portions of said planar insert member are "V" shaped cuts whereby material surrounded by said "V" shaped cuts is lifted out of the plane of said insert member.

7. The suture package according to claim 6 wherein at least two of said "V" shaped cut-out portions are provided on said plastic insert member to retain each needle thereon.

8. The suture package according to claim 7 wherein said at least two of said slits are positioned for respective reception of corner portions of said planar insert member.

9. The suture package according to claim 8 wherein said cut-out portions on said plastic insert member are respectively positioned to retain curved suture needles.

10. The suture package according to claim 9 wherein at least three of said cut-out portions are provided in said plastic insert member to retain each curved suture needle.

11. The suture package according to claim 10 wherein said plastic insert needle retainer is dimensioned and includes sufficient cut-out portions to retain at least two curved suture needles thereon.

12. The suture package according to claim 11 wherein said plastic insert needle retainer is dimensioned and contains sufficient cut-out portions to retain at least five curved needles thereon.

13. A suture package which comprises:
   a) a plurality of panel members foldable connected to each other and arranged to fold upon each other to form at least two individual suture compartments between pairs of adjacent panels; and
   b) a substantially planar insert member formed of a resilient material and attached to one of said panel members and having portions cut and lifted from the plane of the insert member, respective pluralities of said cut portions being dimensioned and positioned to engage respective portions of at least two suture needles to retain such needles in respective fixed positions, whereby such needles are positioned in generally spaced relation and individual flexible suture portions attached to such needles are respectively positioned in individual compartments formed by the remaining adjacent folded panels.

14. The suture package according to claim 13 wherein said planar insert member is retained in position on said one panel member by insertion of marginal portions thereof into slits in said one panel member.

15. The suture package according to claim 14 wherein said planar insert member is of generally rectangular configuration.

16. The suture package according to claim 15 wherein said one panel member contains at least two slits positioned and dimensioned for reception of marginal portions of said planar insert member therein to retain said planar insert member thereon.

17. A suture package which comprises:

a) at least two rows of generally rectangular panels connected to each other and arranged to fold upon each other to form at least two individual suture compartments between pairs of adjacent panels; and b) a substantially planar insert member supported by one of said panel members and having portions cut out and lifted from the plane of the insert member, respective pluralities of said cut portions being dimensioned and positioned to engage respective portions of suture needles to retain such needles in respective fixed positions whereby such needles are positioned in generally spaced relation and individual flexible suture portions are respectively positioned in individual compartments formed by the remaining adjacent folded panels.

18. The suture package according to claim 17 wherein at least one row of said panels contains a plurality of rectangular panels connected to each other on the longitudinal sides thereof.

19. The suture package according to claim 18 wherein the second row includes a plurality of panels connected to each other on the longitudinal sides thereof.

20. The suture package according to claim 19 wherein said at least two rows of panels are respectively connected to each other on the short sides of at least one panel in each row.

21. The suture package according to claim 20 wherein a first row of panels contains at least six panels.

22. The suture package according to claim 21 wherein said second row of panels contains at least three panels.

23. The suture package according to claim 22 wherein at least one of said panels are formed of less material than the others to reduce the girth of the package.

24. The suture package according to claim 22 wherein said three panels of said second row of panels includes a first centrally positioned panel to support said insert member and two adjacent panels foldably connected to said first central panel.

25. The suture package according to claim 24, wherein each panel of said second row is generally rectangular and is connected to the next adjacent panel on a longer side.

26. The suture package according to claim 25 wherein said adjacent panels of said second row are connected to said central panel by a double fold line each of which defines edge panels to encompass said remaining panels in their folded condition.

27. The suture package according to claim 25 wherein at least one panel of said first row is foldably connected to the next adjacent panel by a double fold line to define a second edge panel of width sufficient to encompass said panels and sutures in the folded and assembled condition.

28. A suture package which comprises:

a) a first row of a plurality of generally rectangular panels foldably connected to each other on the longitudinal sides thereof and arranged to fold upon each other to form at least two individual suture compartments between pairs of adjacent panels, each said panel containing at least four notches, at least two notches on at least one panel facing the notches on the next adjacent panel in the same row, in their folded condition, said notches being dimensioned and positioned for reception of suture winding pins therethrough for winding the flexible suture portions therearound;

b) a second row of a plurality of generally rectangular panels foldably connected to each other on the longitudinal sides thereof;

c) needle holding means associated with one of said panels of said second row of panels to retain at least two suture needles in respective fixed positions on said one panel whereby said needles are positioned in generally spaced relation and individual flexible suture portions are respectively positioned in said individual suture compartments formed by the remaining adjacent folded panels; and d) said first row of panels being connected to said second row of panels on the short sides of at least one panel in each row.

29. The suture package according to claim 28 wherein at least one of said panels of said first row contains an end flap on a short side.

30. The suture package according to claim 29 wherein said end flap has a generally tapered end portion and said end flap is adapted to be folded over one shorter side to protect the sutures.

31. A suture package which comprises:

a) a first row of a plurality of generally rectangular panels foldably connected to each other on the longitudinal sides thereof and arranged to fold upon each other to form at least two individual sutures compartments between pairs of adjacent panels;

b) a second row of a plurality of generally rectangular panels foldably connected to each other on the longitudinal sides thereof, said second row of panels including a first centrally positioned panel and two adjacent panels foldably connected to said first central panel, said central panel supporting a plastic needle insert with at least two needles being supported thereof, a first flexible suture portion connected to a first needle and being wound in a coiled configuration and positioned between a first panel and the next adjacent second panel of said first row, and, a second flexible suture portion connected to a second needle being positioned in coiled configuration between said second panel and the next adjacent third panel of said first row; and c) said first row of panels being connected to said second row of panels on the shorter sides of at least one panel in each row.

32. The suture package according to claim 31 wherein said second row of folded panels is folded along said shorter side defining a fold line between said panels of each row of panels, said adjacent panels of said second row being respectively folded around the folded panels and sutures.

33. The suture package according to claim 32 wherein said adjacent panels of said second row of panels include means for connecting said panels together.

34. The suture package according to claim 33 wherein said connecting means in said adjacent panels of said second row comprise at least two slots in one of said end panels and at least two arcuate cuts in said other end panel to define arcuate tabs, said arcuate tabs being positioned and dimensioned for entry into said slots in said other adjacent panel to retain said panels in closed positions about said panels of said first row and said sutures positioned therebetween.

35. The suture package according to claim 34 wherein certain of said panels each define at least one aperture to reduce the girth of the package when fully loaded.

36. The suture package according to claim 35 wherein certain of said panels define apertures to permit introduction of fluid into the compartments defined thereby.

37. A suture package which comprises:
 a) a first row of a plurality of generally rectangular shaped panels connected to each other by fold lines along the longer sides thereof;
 b) a second row of at least three generally rectangular shaped panels connected to each other by fold lines along the longer sides thereof, one of said panels of said second row being a connector panel connected to a panel of said first row by a fold line along the shorter sides thereof;
 c) needle retaining means associated with said connector panel of said second row; and
 d) said panels of said first row being respectively foldable in a manner independent from said panels of said second row to form compartments between adjacent panels, each compartment adapted to contain at least one flexible suture portion therein in a wound configuration, each suture attached to a needle held by said needle retaining means, said panels being finally foldable to form a generally rectangular suture package.

38. The suture package according to claim 37 wherein said needle retaining means comprises an insert member having portions cut out and lifted from the plane of the insert, respective pluralities of said cutout portions being dimensioned and positioned to engage respective portions of said suture needles.

39. The suture package according to claim 38 wherein said planar insert member is of resilient material.

40. The suture package according to claim 39 wherein said resilient material is plastic.

41. The suture package according to claim 38 wherein said planar insert member is retained in position on said central panel member of said second row by insertion of marginal portions thereof into slits in said central panel member.

42. The suture package according to claim 41 wherein said planar insert member is of generally rectangular configuration.

43. The suture package according to claim 42 wherein said central panel member contains at least four slits positioned and dimensioned for reception of corner portions of said insert member therein to retain said insert member thereon.

44. The suture package according to claim 43 wherein said cut-out portions of said plastic insert member are "V" shaped cuts whereby material surrounded by said "V" shaped cuts is lifted out of the plane of said insert member.

45. The suture package according to claim 38 wherein at least two of said "V" shaped cut-out portions are provided on said plastic insert member to retain each needle thereon.

46. The suture package according to claim 45 wherein said cut-out portions on said plastic insert member are respectively positioned to retain curved suture needles.

47. The suture package according to claim 46 wherein at least three of said cut-out portions are provided in said plastic insert member to retain each curved suture needle.

48. The suture package according to claim 47 wherein said plastic insert needle retainer is dimensioned and includes sufficient cut-out portions to retain at least two curved suture needles thereon.

49. The suture package according to claim 47 wherein said plastic insert needle retainer is dimensioned and contains sufficient cut-out portions to retain at least five curved needles thereon.

50. The suture package according to claim 37 wherein said at least two rows of panels are respectively connected to each other by an intermediate panel, said intermediate panel attached to the short sides of one panel in each row.

51. The suture package according to claim 37 wherein said first row contains at least six panels.

52. The suture package according to claim 51 wherein at least two panels of said first row have a generally central portion cut away to reduce the girth of the combined sutures and panels.

53. The suture package according to claim 51 wherein the lengths of at least two of said panels of said first row of panels are approximately one-half the lengths of the remaining panels to reduce the girth of the package when the panels are fully folded.

54. The suture package according to claim 53 wherein said first row of panels possesses three such half panels.

55. The suture package according to claim 54 wherein at least one of said panels of said first row contains an end flap on a shorter side.

56. The suture package according to claim 54 wherein said shorter panels are connected to each other and one longer panel is connected to one end of said shorter panels on one side of said row and two of said longer panels are connected to another of said shorter panels on the opposite side.

57. The suture package according to claim 56, wherein said one longer end panel has an end flap connected to a shorter side thereof such that when said panels are respectively folded with a plurality of needles positioned in the compartment and the flexible suture portions connected thereto respectively positioned in individual compartments formed by adjacent panels, said end flap is foldable over said needle compartment to cover and protect the upper end portions of said needles.

58. The suture package according to claim 37 wherein said plurality of panels of said first row have apertures configured to receive pins for winding sutures thereof.

59. The suture package according to claim 58 wherein said apertures have a generally tapered configuration.

60. The suture package according to claim 59 wherein said tapered apertures extend across the fold line between adjacent panels.

61. The suture package according to claim 59 wherein at least five panels of said first row each contain two tapered apertures.

62. The suture package according to claim 37 wherein at least one panel on said first row contains a circular aperture to permit fluid to be added to said package.

63. The suture package according to claim 37 wherein at least one of said panels of said second row contains an end flap foldably connected along a shorter side.

64. The suture package according to claim 37 wherein an end panel is connected to one end panel of said second row such that when said panels are respectively folded within a plurality of needles positioned in said needle retaining means and the flexible suture portions connected thereto are respectively positioned in individual compartments formed by folded adjacent connected panels of said first row, said end flap is foldable over said needle compartment to cover and protect the upper end portions of said needles.

65. A suture package which comprises:
   a) a plurality of panel members foldably connected to each other and arranged to fold upon each other to form a suture compartment between pairs of adjacent panels, at least two panel members having a generally central portion cut away to reduce the girth of the combined sutures and panels; and
   b) a generally planar insert member having portions cut out and lifted from the plane of the insert, respective pluralities of said cut portions being dimensioned and positioned to engage respective portions of at least two suture needles positioned thereon to retain said needles in respective fixed position within the package whereby said needles are positioned in generally spaced relation in one compartment and individual flexible suture portions are respectively positioned in individual compartments formed by the remaining adjacent folded panels.

66. The suture package according to claim 65 wherein each panel member has a generally central portion cut away to reduce the girth of the combined sutures and panels.

67. A suture package which comprises:
   a) a first row of six generally rectangular shaped panels connected to each other by fold lines along the longer sides;
   b) a second row of three generally rectangular shaped panels connected to each other by fold lines along the longer sides, the central panel of said second row being connected to a second panel of said first row by a fold line along the shorter sides thereof, said central panel of said second row defining a plurality of cuts for reception of a generally rectangular needle retainer panel;
   c) a flexible plastic needle retainer panel attached to said central panel of said second row by insertion of the corner portions thereof into said cuts in said panel and having a plurality of "V" shaped cut-outs adapted to be defined out of the plane of said insert for retaining five curved suture needles thereon; and
   d) said panels being respectively folded in a manner to form compartments between adjacent panel, each compartment containing at least one flexible suture portion therein in a wound configuration, said panels being finally folded to form a generally rectangular suture package.

68. The suture package according to claim 67 wherein said flexible suture portions are each wound in their respective compartment in a Figure "8" configuration.

69. The suture package according to claim 68 wherein an end flap is connected to at least one of said panels and adapted to be folded over said needles when positioned on said needle retainer panel, said end flap dimensioned and configured to cover and protect at least the needle portion connecting the flexible suture portions.

70. The suture package according to claim 69 wherein said first row is connected to said second row by two panels foldably connected to each other, each said panel connected to each respective row along a fold line.

71. A method of loading a suture package with a plurality of sutures, each suture having a flexible suture portion and a surgical needle attached to one end, said suture package having a first row of generally rectangular shaped panels connected to each other along fold lines extending along the longer sides thereof, a second row of generally rectangular shaped panels connected to said first row, said panels of said second row being connected to each other along fold lines extending along the longer sides thereof, and a needle retainer panel attached to at least one of said panels of said second row for releasably retaining the surgical needles in spaced relation, comprising:
   a) positioning at least two of said needles on said needle retainer panel;
   b) aligning the panels of said first row opposite said needle retainer panel on the winding fixture such that winding pins thereof extend upwardly adjacent said panel of said second row;
   c) winding the flexible suture portion connected to the first needle about the winding pins until the suture portion is coiled upon itself within the periphery of said panel;
   d) folding the next adjacent panel of said second row over said coiled suture portion;
   e) winding the flexible suture portion attached to the next adjacent needle about said winding pins until the suture portion is coiled within the periphery of said folded panel; and
   f) repeating steps a), b), c) and d) sufficient to position each needle and to coil and position each flexible suture portion within a respective compartment defined by adjacent panels.

72. The method of loading a suture package according to claim 71 wherein an end flap is connected to one panel of said first row and said steps are followed by folding said end flap over the suture connecting portion of the needles to cover and protect the needles.

73. A method of loading a suture package with a plurality of sutures, each suture having a flexible suture portion and a surgical needle attached to one end, said suture package having a first row of generally rectangular shaped panels connected to each other along fold lines extending along the longer sides thereof, a second row of generally rectangular shaped panels connected to said first row, said panels of said second row being connected to each other along fold lines extending along the longer sides thereof, a needle retainer panel attached to at least one of said panels of said second row for releasably retaining the surgical needles in spaced relation, and a needle protective end flap connected to the shorter side of at least one of said rectangular panels, the method comprising the steps of:
   a) positioning at least two of said needles on said needle retainer panel;
   b) aligning the panels of said first row opposite said needle retainer panel on the winding fixture such that winding pins thereof extend upwardly adjacent said panel of said second row;

c) winding the flexible suture portion connected to the first needle about the winding pins until the suture portion is coiled upon itself within the periphery of said panel;

d) folding the next adjacent panel of said second row over said coiled suture portion;

e) winding the flexible suture portion attached to the next adjacent needle about said winding pins until the suture portion is coiled within the periphery of said folded panel;

f) repeating steps a), b), c) and d) sufficient to position each needle and to coil and position each flexible suture portion within a respective compartment defined by adjacent panels; and g) folding said end flap over the suture connecting portion of the needles to cover and protect the needles.

74. A method of loading a suture package with a plurality of needled sutures into a suture package on a suture wrapping fixture having upstanding suture winding pins wherein said suture package includes a first row of generally rectangular shaped panels connected to each other by fold lines along the longer sides, a second row of generally rectangular shaped panels connected to said first row, said panels of said second row being connected to each other by fold lines along the longer sides, the central panel of said second row being connected to a second panel of said first row by a fold line along the shorter sides thereof, said central panel of said second row having means to attachment of a needle retainer panel;

a needle retainer panel attached to said central panel of said second row and adapted to removably retain a plurality of needles comprising:

a) securing said first curved needle to a first group of "V" shaped cuts of said needle retainer panel and winding the flexible suture portion onto the second panel of said first row of panels;

b) folding a third panel of said first row of panels onto said second panel to form a compartment for the flexible suture portion wound on said second panel;

c) securing said second curved needle to a second group of "V" shaped cuts of said needle retainer panel and winding the flexible suture portion thereof onto the rear side of said third panel of said first row of panels; d) folding a fourth panel of said first row of panels onto said third panel to form a compartment for the flexible portion suture wound on said third panel;

e) securing said third curved needle to a third group of "V" shaped cuts of said needle retainer panel and winding the flexible suture portion onto the fourth panel of said first row of panels;

f) folding a first panel of said first row of panels onto said fourth panel to form a compartment for the flexible suture portion wound on said fourth panel;

g) securing said fourth curved needle to a fourth group of "V" shaped cuts of said needle retainer panel and winding the flexible suture portion onto the rear side of said first panel of said first row of panels;

h) folding a fifth panel of said first row of panels onto said first panel to form a compartment for the flexible suture portion wound on said first panel;

i) securing said fifth curved needle to a fifth group of "V" shaped cuts of said needle retainer panel and winding the flexible suture onto the rear side of said fifth panel of said first row of panels;

j) folding a sixth panel of said first row of panels onto said fifth panel to form a compartment for the suture wound on said fifth panel;

k) folding said second row of panels onto said first row of panels along said fold line connecting said first and second row;

l) folding a third panel of said second row of panels onto said folded first row of panels;

m) folding a first panel of said second row of panels onto said folded first row of panels and onto said third panel of said second row; and n) securing said first panel of said second row to said third panel of said second row to form said fully folded suture package.

75. The method of loading a suture package according to claim 74 wherein an end flap is connected to one panel of said second row and said steps are followed by folding said end flap over the suture connecting portion of the needles to cover and protect the needles.

76. A suture package which comprises:

a) a first row of a plurality of generally rectangular shaped panels connected to each other by fold lines along the longer sides thereof, at least two panels having a generally central portion cut away to reduce the girth of the combined sutures and panels when the package is in a folded condition;

b) a second row of at least three generally rectangular shaped panels connected to each other by fold lines along the longer sides thereof, at least one panel of said second row being a connector panel connected to a panel of said first row by a fold line along the shorter sides thereof;

c) needle retaining means attached to said connector panel of said second row; and d) said panels of said first row being respectively foldable in a manner to form compartments between adjacent panels, each compartment adapted to contain at least one flexible suture portion therein in a wound configuration, each suture attached to a needle held by said needle retaining means, said panels being finally foldable to form a generally rectangular suture package.

77. A suture package which comprises:

a) a first row of a plurality of generally rectangular shaped panels connected to each other by fold lines along the longer sides thereof, at least two of said panels being approximately one-half the length of the remaining panels to reduce the girth of the package when the panels are in the fully folded condition.

b) a second row of at least three generally rectangular shaped panels connected to each other by fold lines along the longer sides thereof, at least one of said panels of said second row being a connector panel connected to a panel of said first row by a fold line along the shorter sides thereof;

c) needle retaining means associated with said connector panel of said second row; and d) said panels of said first row being respectively foldable in a manner to form compartments between adjacent panels, each compartment adapted to contain at least one flexible suture portion therein in a wound configuration, each suture attached to a needle held by said needle retaining means, said panels being finally foldable to form a generally rectangular suture package.

78. A suture package which comprises:
a) a first row of a plurality of generally rectangular shaped panels connected to each other by fold lines along the longer sides thereof;
b) a second row of at least three generally rectangular shaped panels connected to each other by fold lines along the longer sides thereof, one of said panels of said second row being a connector panel connected to a panel of said first row by a fold line along the shorter sides thereof;
c) an end flap foldably connected to a shorter side of at least one of said panels of said second row;
d) needle retaining means associated with said connector panel of said second row; and
e) said panels of said first row being respectively foldable in a manner independent from said panels of said second row to form compartments between adjacent panels, each compartment adapted to containing at least one flexible suture portion therein in a wound configuration, each suture attached to a needle held by said needle retaining means, said panels being finally foldable to form a generally rectangular suture package.

79. A suture package which comprises: 'a) a first row of generally rectangular shaped panels connected to each other by fold lines along the longer sides thereon, said panels having apertures to receive pins for winding sutures therein, each said apertures having a generally tapered configuration and extending across the fold line between adjacent panels;
b) a second row of at least three generally rectangular shaped panels connected to each other by fold lines along the longer sides thereof, one of said panels of said second row being a connector panel connected to a panel of said first row by a fold line along the shorter sides thereof;
c) needle retaining means associated with said connector panel of said second row; and
d) said panels of said first row being respectively foldable in a manner independent from said panels in said second row to form compartments between adjacent panels, each compartment adapted to contain at least one flexible suture portion therein in a wound configuration, each suture attached to a needle held by said needle retaining means, said panels being finally foldable to form a generally rectangular suture package.

80. A suture package which comprises:
a) a plurality of panel members foldably connected to each other and arranged to fold upon each other to form at least two individual suture compartments between pairs of adjacent panels; and
b) a substantially planar insert member formed of a resilient material and attached to one of said panel members and having portions cut and lifted from the plane of the insert member, respective pluralities of said cut portions being dimensioned and positioned to engage respective portions of at least two suture needles to retain such needles in respective fixed positions, wherein such needles are positioned in generally spaced relation and individual flexible suture portions attached to such needles are each individually wound and positioned in a separate suture compartment formed by adjacent panels folded upon each other.

81. A suture package for storing a plurality of flexible suture portions, each having at least one needle attached thereto, which comprises:
a) a plurality of panel members foldably connected to each other and arranged to fold upon each other to form at least two individual suture compartments between pairs of adjacent panels; and
b) a needle holding insert sheet attached to one of said panel members and adapted to retain all such suture needles in respective fixed spaced positions whereby all such needles may be positioned in generally spaced relation on said insert sheet and the individual flexible suture portions are respectively positioned in said individual suture compartments formed by the remaining adjacent folded panels.

* * * * *